US010499965B2

(12) United States Patent
Paik

(10) Patent No.: US 10,499,965 B2
(45) Date of Patent: *Dec. 10, 2019

(54) FIXING MECHANISM FOR CLOSED DISTAL FEMUR OSTEOTOMY

(71) Applicant: Hae Sun Paik, Seoul (KR)

(72) Inventor: Hae Sun Paik, Seoul (KR)

( * ) Notice: Subject to any disclaimer, the term of this patent is extended or adjusted under 35 U.S.C. 154(b) by 372 days.

This patent is subject to a terminal disclaimer.

(21) Appl. No.: 15/532,481

(22) PCT Filed: Oct. 28, 2015

(86) PCT No.: PCT/KR2015/011459
§ 371 (c)(1),
(2) Date: Jun. 1, 2017

(87) PCT Pub. No.: WO2016/089012
PCT Pub. Date: Jun. 9, 2016

(65) Prior Publication Data
US 2017/0325860 A1    Nov. 16, 2017

(30) Foreign Application Priority Data
Dec. 3, 2014   (KR) ........................ 10-2014-0172255

(51) Int. Cl.
*A61B 17/80*    (2006.01)
*A61B 17/74*    (2006.01)

(52) U.S. Cl.
CPC .......... *A61B 17/8061* (2013.01); *A61B 17/74* (2013.01); *A61B 17/8057* (2013.01); *A61B 17/8095* (2013.01)

(58) Field of Classification Search
CPC ....................................... A61B 17/74–17/8095
See application file for complete search history.

(56) References Cited

U.S. PATENT DOCUMENTS 7,153,309 B2 *   12/2006   Huebner ............ A61B 17/1728
                                                    606/96
7,578,825 B2 *   8/2009    Huebner ............. A61B 17/683
                                                    606/104
(Continued)

FOREIGN PATENT DOCUMENTS

EP         1719469 A1    11/2006
JP      2007500069 A     1/2007
(Continued)

OTHER PUBLICATIONS

International Search Report for PCT/KR2015/011459 filed on Oct. 28, 2015.
(Continued)

*Primary Examiner* — Zade Coley
(74) *Attorney, Agent, or Firm* — STIP Law Group, LLC

(57) ABSTRACT

A fixing mechanism for a closed distal femur osteotomy according to an exemplary embodiment of the present invention is installed on a femur incised by the closed distal femur osteotomy, and the fixing mechanism includes: a body portion which is in close contact with the femur and has a plurality of coupling holes and an oblong hole; a head portion which is connected to one end of the body portion and has a plurality of coupling holes; screws which are inserted into the coupling holes; and a sliding screw which is inserted into the oblong hole by adjusting a coupling position, in which the head portion has a predetermined inclination angle in an upward direction based on a lower surface of the head portion.

10 Claims, 5 Drawing Sheets

(56) References Cited

U.S. PATENT DOCUMENTS

| | | | |
|---|---|---|---|
| 7,603,192 B2* | 10/2009 | Martin | A61B 17/8061 700/98 |
| 7,722,653 B2* | 5/2010 | Young | A61B 17/8014 606/280 |
| 8,177,819 B2* | 5/2012 | Huebner | A61B 17/80 606/281 |
| 8,267,972 B1 | 9/2012 | Gehlert | |
| 8,382,807 B2* | 2/2013 | Austin | A61B 17/74 606/293 |
| 8,425,574 B2* | 4/2013 | Huebner | A61B 17/1728 606/281 |
| 8,425,575 B2* | 4/2013 | Huebner | A61B 17/8061 606/102 |
| 8,454,665 B2* | 6/2013 | Sidebotham | A61B 17/8863 606/280 |
| 8,523,919 B2* | 9/2013 | Huebner | A61B 17/1728 606/280 |
| 8,523,921 B2* | 9/2013 | Horan | A61B 17/8061 606/291 |
| 8,617,161 B2* | 12/2013 | Ferrante | A61B 17/164 606/62 |
| 8,641,744 B2 | 2/2014 | Weaver et al. | |
| 8,652,180 B2* | 2/2014 | Federspiel | A61B 17/1728 606/281 |
| 8,858,602 B2* | 10/2014 | Weiner | A61B 17/151 606/282 |
| 9,138,244 B2* | 9/2015 | Mebarak | A61B 17/1728 |
| 10,143,503 B2* | 12/2018 | Kuroda | A61B 17/8061 |
| 10,299,841 B2* | 5/2019 | Dunlop | A61B 17/80 |
| 2004/0102778 A1* | 5/2004 | Huebner | A61B 17/1728 606/71 |
| 2005/0015089 A1* | 1/2005 | Young | A61B 17/8014 606/915 |
| 2005/0234472 A1* | 10/2005 | Huebner | A61B 17/683 606/104 |
| 2005/0240187 A1* | 10/2005 | Huebner | A61B 17/80 606/71 |
| 2007/0173840 A1* | 7/2007 | Huebner | A61B 17/80 606/304 |
| 2007/0233106 A1* | 10/2007 | Horan | A61B 17/8061 606/282 |
| 2008/0051791 A1* | 2/2008 | Young | A61B 17/8014 606/250 |
| 2008/0195240 A1* | 8/2008 | Martin | A61B 17/8061 700/98 |
| 2008/0275562 A1* | 11/2008 | Clifford | A61B 17/68 623/20.21 |
| 2008/0300637 A1* | 12/2008 | Austin | A61B 17/74 606/290 |
| 2009/0234359 A1* | 9/2009 | Onoue | A61B 17/8605 606/71 |
| 2010/0152783 A1* | 6/2010 | Borostyankoi | A61B 17/8014 606/281 |
| 2010/0274296 A1* | 10/2010 | Appenzeller | A61B 17/8605 606/305 |
| 2010/0324602 A1* | 12/2010 | Huebner | A61B 17/80 606/280 |
| 2011/0137351 A1* | 6/2011 | Huebner | A61B 17/1728 606/286 |
| 2012/0078252 A1* | 3/2012 | Huebner | A61B 17/1728 606/70 |
| 2012/0078311 A1* | 3/2012 | Huebner | A61B 17/8061 606/281 |
| 2012/0078312 A1* | 3/2012 | Federspiel | A61B 17/1728 606/281 |
| 2012/0265254 A1* | 10/2012 | Horan | A61B 17/8061 606/289 |
| 2013/0296943 A1* | 11/2013 | Grady, Jr. | A61B 17/746 606/291 |
| 2014/0163621 A1* | 6/2014 | Huebner | A61B 17/1728 606/281 |
| 2015/0127011 A1* | 5/2015 | Dunlop | A61B 17/80 606/88 |
| 2017/0007304 A1* | 1/2017 | Kuroda | A61B 17/8061 |

FOREIGN PATENT DOCUMENTS

| | | |
|---|---|---|
| JP | 2007505682 A | 3/2007 |
| JP | 2011189174 A | 9/2011 |
| KR | 10-2006-0035604 A | 4/2006 |
| KR | 10-2006-0115603 A | 11/2006 |
| KR | 10-2007-0031841 A | 3/2007 |
| KR | 10-2008-0107390 A | 12/2008 |
| WO | 2007100513 A2 | 9/2007 |
| WO | 2012003884 A1 | 1/2012 |

OTHER PUBLICATIONS

Extended European Search Report for EP Application No. 15866206.4 dated Jun. 13, 2018.

* cited by examiner

FIXING MECHANISM FOR CLOSED DISTAL FEMUR OSTEOTOMY

This application is a U.S. National Stage of PCT/KR2015/011459, filed Oct. 28, 2015, which claims the priority benefit of Korean Patent Application No. 10-2014-0172255 filed on Dec. 3, 2014, in the Korean Intellectual Property Office, the disclosures of which are incorporated herein by reference.

TECHNICAL FIELD

The present invention relates to a fixing mechanism for a distal femur osteotomy. More particularly, the present invention relates to a fixing mechanism for a distal femur osteotomy which ensures secure fixing force by fixing a plate after a closed distal femur osteotomy.

BACKGROUND ART

In general, in the case of degenerative arthritis, legs are deformed to 'X'-shaped legs as the knees are bent outward, and in some instances, an arrangement of knee joints is abnormally deformed due to an innate factor, an acquired factor caused by life habits, or other diseases such as a fracture or an avascular necrosis caused previously.

In this case, there is a knee joint osteotomy as one of the surgical methods, and the knee joint osteotomy is a treatment method which corrects an abnormal axis of a lower limb and shifts a load, which is applied to a knee joint, to a more healthy joint surface, thereby improving a distribution of stress and a joint alignment, and thus improving pain.

Unlike artificial knee joint replacement, the knee joint osteotomy is a method capable of preserving the joint and has an advantage in that an artificial joint surgery time may be delayed, and a joint movement range may be maintained to be almost similar to a joint movement range before the surgery.

A distal femur osteotomy, which is an example of the knee joint osteotomy, is performed by cutting a predetermined amount of bone, removing the bone by the amount corresponding to a necessary angle, bonding the bone, and fixing the incised bone by using a plate and screws.

However, the plate in the related art does not match with Korean body types, and angles at an osteotomy site are misaligned, and as a result, there is a problem in that complications are caused after the surgery.

DOCUMENT OF RELATED ART

Korean Patent No. 10-0916334

DISCLOSURE

Technical Problem

An exemplary embodiment of the present invention provides a fixing mechanism for a distal femur osteotomy which is capable of having secure coupling force by rotating a head portion of a plate.

In addition, an exemplary embodiment of the present invention provides a fixing mechanism for a distal femur osteotomy in which an angle is formed at a head portion so that screws are not withdrawn from a bone.

Technical Solution

A fixing mechanism for a closed distal femur osteotomy according to an exemplary embodiment of the present invention is installed on a femur incised by the closed distal femur osteotomy, and the fixing mechanism may include: a body portion which is in close contact with the femur and has a plurality of coupling holes and an oblong hole; a head portion which is connected to one end of the body portion and has a plurality of coupling holes; screws which are inserted into the coupling holes; and a sliding screw which is inserted into the oblong hole by adjusting a coupling position, in which the head portion has a predetermined inclination angle in an upward direction based on a lower surface of the head portion.

Particularly, the head portion may be twisted in a left or right direction based on the body portion and coupled to the body portion.

Particularly, the coupling holes may be formed in the head portion along a plurality of rows, and the plurality of coupling holes may be formed at each of the rows.

Particularly, the head portion and the body portion may be formed to be curved and be in close contact with the femur.

Particularly, the screws coupled to the head portion may be coupled to be directed toward a particular point.

Particularly, a line, which connects central portions of the coupling holes formed along a first row on an upper surface of the head portion, may be inclined 3 to 5 degrees based on a reference line.

Particularly, a line, which connects central portions of the coupling holes formed along a first row on a lower surface of the head portion, may be inclined 5 to 7 degrees based on the reference line.

Particularly, a line, which connects central portions of the coupling holes formed along a second row on the lower surface of the head portion, may be inclined 1.5 to 2.5 degrees based on the reference line.

Particularly, one surface of the head portion may have an inclination angle of 20 to 22 degrees based on the body portion, and the other surface of the head portion may have an inclination angle of 24 to 26 degrees based on the body portion.

Particularly, one surface of the body portion may have a predetermined inclination based on a lateral surface of the head portion.

Particularly, the body portion may have an angle of 7 to 9 degrees.

Particularly, two coupling holes may be formed along each of the plurality of rows, the screw, which is inserted into the coupling hole formed in a first row, may have an inclination angle of 13 to 15 degrees based on a reference line, and the screw, which is inserted into the coupling hole formed in a second row, may have an inclination angle of 17 to 19 degrees based on the reference line.

Particularly, at least one guide hole to which a guide pin is fixed may be formed in the head portion or the body portion.

Particularly, two coupling holes may be formed along each of the plurality of rows, and the screw, which is inserted into the coupling hole formed in a second row, may be inclined 16 to 18 degrees based on a vertical line.

Advantageous Effects

According to the fixing mechanism for a distal femur osteotomy according to the exemplary embodiment of the present invention, it is possible to securely couple the plate and the bone by rotating the head portion.

In addition, since angles are formed at the head portion and thus the screws are not withdrawn from the bone, it is possible to reduce complications after the surgery.

BEST MODE

Figure 1:
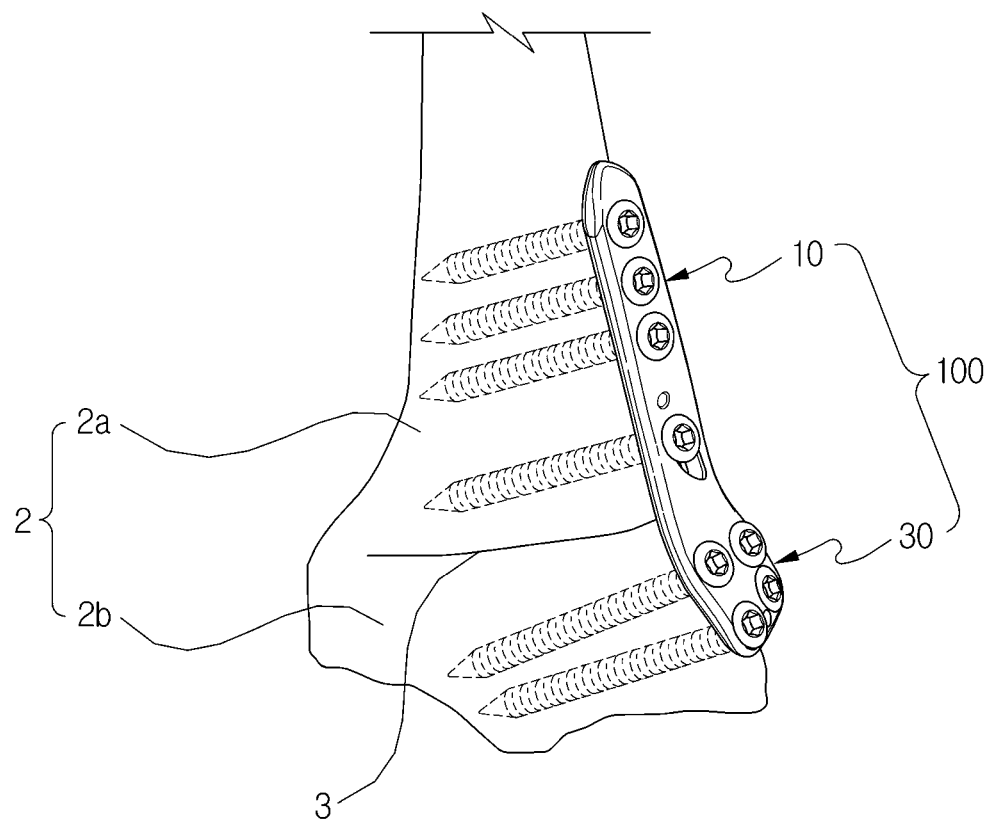
FIG. 1 is a view illustrating a state in which a fixing mechanism for a distal femur osteotomy according to an exemplary embodiment of the present invention is coupled to a femur.

Hereinafter, a fixing mechanism for a distal femur osteotomy according to an exemplary embodiment of the present invention will be described in detail with reference to the accompanying drawings. First, in denoting reference numerals to constituent elements of the respective drawings, it should be noted that the same constituent elements will be designated by the same reference numerals, if possible, even though the constituent elements are illustrated in different drawings. Further, an exemplary embodiment of the present invention will be described below, but the technical spirit of the present invention is not limited thereto and may be modified and variously carried out by those skilled in the art.

FIG. 1 is a view illustrating a state in which a fixing mechanism for a distal femur osteotomy according to an exemplary embodiment of the present invention is coupled to a femur.

Referring to FIG. 1, a femur 2 is divided into an upper femur 2a and a lower femur 2b based on cut surfaces 3 which are cut by a distal femur incision procedure for incising the femur 2.

A fixing mechanism 1 for a closed distal femur osteotomy according to the exemplary embodiment of the present invention may include a body portion 10 which is in close contact with the femur 2 and has a plurality of coupling holes 14 and an oblong hole 16, a head portion 30 which is connected to one end of the body portion 10 and has a plurality of coupling holes 34, screws 12 and 32 which are inserted into the coupling holes 14 and 34, and a sliding screw 54 which is inserted into the oblong hole 16.

A plate 100 may include the body portion 10 and the head portion 30, and may have the plurality of coupling holes 14 and 34 into which the screws 12 and 32 to be fixed to the femur 2 are inserted.

The body portion 10 may be formed in an elongated shape, and the plurality of coupling holes 14 may be formed in a longitudinal direction of the body portion 10. The coupling holes 14 formed in the body portion 10 are formed at predetermined intervals so as to uniformly distribute supporting force. The screws 12 and 32, which penetrate the coupling holes 14 formed in the body portion 10, may be coupled to the upper femur 2a at a right angle to the upper femur 2a. A length of each of the screws 12 and 32 coupled to the body portion 10 may be variously modified in accordance with a diameter of the upper femur 2a.

The sliding screw 54 may be coupled to the oblong hole 16 formed in the body portion 10. A bone is cut as much as needed for a distal femur osteotomy procedure, and the cut surfaces 3 are connected to each other in order to correct an abnormal axis of a lower limb. In this case, the cut surface 3 may not be formed at a predetermined position. The sliding screw 54 is coupled to the oblong hole 16, and the sliding screw 54 may be coupled to the femur 2 by being moved in accordance with a position of the cut surface 3. The sliding screw 54 may be inserted into the upper femur 2a so as not to penetrate the cut surface 3.

Figure 2:
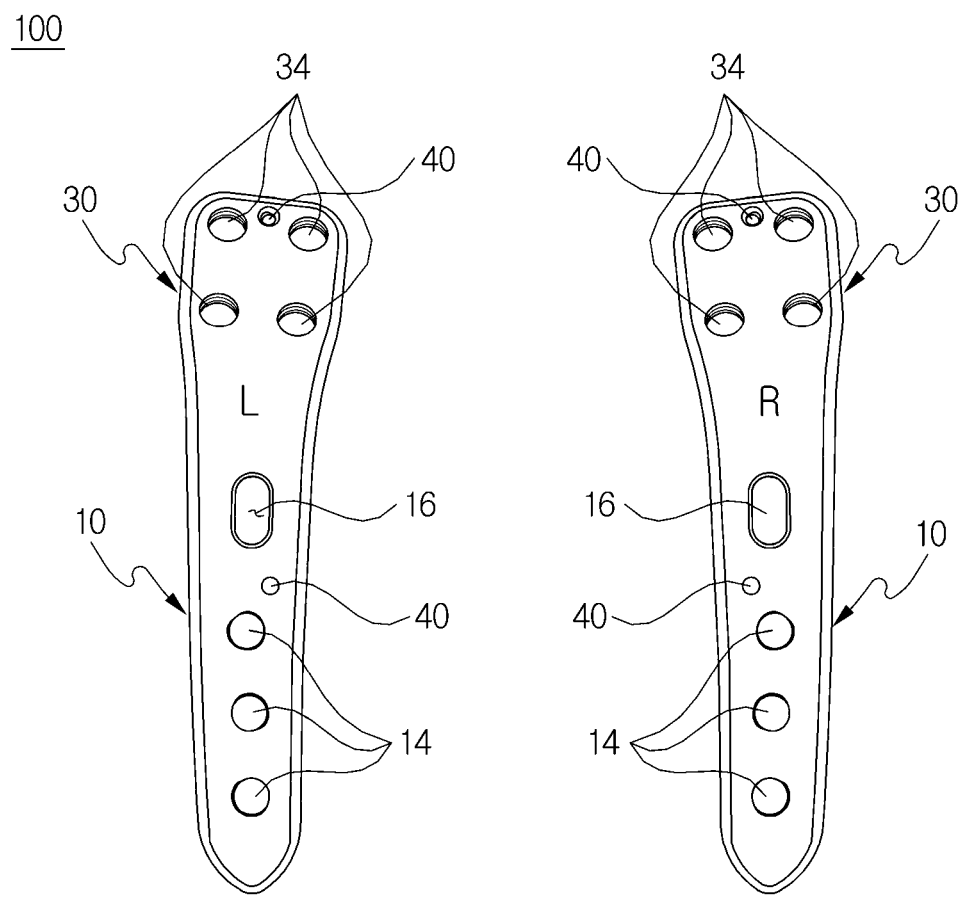
FIG. 2 is a view illustrating a shape of a plate which is a constituent element of the present invention.
Figure 3:
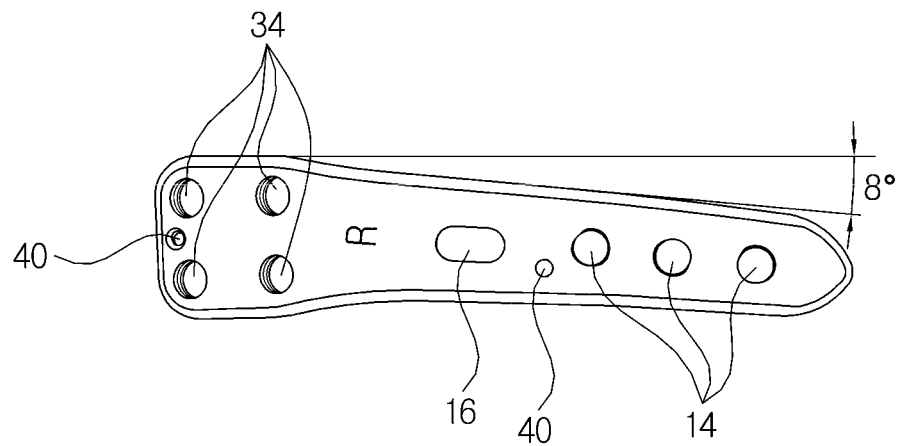
FIG. 3 is a view illustrating a coupling angle at which a body portion and a head portion of the plate in FIG. 2 are coupled.

FIG. 2 is a view illustrating a shape of the plate which is a constituent element of the present invention, and FIG. 3 is a view illustrating an angle of the body portion which is a constituent element of the present invention.

Referring to FIGS. 2 and 3, the plate 100 of the fixing mechanism 1 for a closed distal femur osteotomy according to the exemplary embodiment of the present invention may be classified into a left-hand plate and a right-hand plate in accordance with a surgical site, and the left-hand plate and the right-hand plate define a symmetrical structure.

The body portion 10 is coupled to the upper femur 2a, and may have an elongated shape. As an exemplary embodiment, the body portion 10 may be formed such that a width of the body portion 10 is increased in a direction from the upper femur 2a to the cut surface 3. The reason is to stably support a load when the body portion 10 is coupled to the cut surface 3.

The plurality of coupling holes 14 and 34 formed in the body portion 10 may be provided in the longitudinal direction of the body portion 10. The coupling holes 14 and 34 formed in the body portion 10 are formed at predetermined intervals, and the screws 12 and 32 are inserted into the coupling holes 14 and 34, thereby stably supporting the surgical site.

The oblong hole 16 may be formed at one end of the body portion 10, that is, at a side where the body portion 10 is coupled to the head portion 30. The oblong hole 16 is formed in the longitudinal direction of the body portion 10, thereby allowing a position of the sliding screw 54 to be adjusted when the sliding screw 54 is coupled to the oblong hole 16. The oblong hole 16 allows a coupling position to be adjusted, thereby enabling the plate 100, which is ergonomically designed, to come into close contact with the femur 2, and enabling the plate 100 to stably support a load.

The head portion 30 is connected to one end of the body portion 10, and may have the plurality of coupling holes 34. The head portion 30 is formed to be wider in width than the body portion 10, and may be coupled to the lower femur 2b.

The coupling holes 34 formed in the head portion 30 may be formed along a plurality of rows and a plurality of columns, and the screws 32 are inserted into the coupling holes 34, respectively, thereby fixing the plate 100 to the lower femur 2b.

As an exemplary embodiment, the coupling holes 34 formed in the head portion 30 are formed along the plurality of rows, and the plurality of coupling holes 34 may be formed along the rows, respectively. Particularly, the coupling holes 34 formed in the head portion 30 may be formed along two rows and two columns. The arrangement of the coupling holes 34 may be variously modified in accordance with a shape of the head portion 30.

The body portion 10 and the head portion 30 are divided as necessary, but the body portion 10 and the head portion 30 may be integrally formed. A thickness of each of the body portion 10 and the head portion 30 may be 4 to 6 mm, particularly, 5 mm. A thickness of each of the body portion 10 and the head portion 30 may be variously modified in accordance with an age and a thickness of a bone of a patient subjected to the surgery.

A lateral surface of the body portion 10 may form a predetermined angle based on a lateral surface of the head portion 30. As an exemplary embodiment, an angle, which is formed by the lateral surface of the body portion 10 based on the lateral surface of the head portion 30, may be 7 to 9 degrees. The reason why the body portion 10 has a predetermined angle based on the head portion 30 is to couple the plate 100 to the femur 2 so that the plate 100 is in close contact with the femur 2. The angle formed by the body portion 10 is just an example, and may be variously modified.

At least one guide hole 40 to which a guide pin (not illustrated) is fixed may be formed in the plate 100. The plate 100 may be temporarily fixed by installing the guide pin (not illustrated) before inserting the screws 12 and 32.

The reason is to prevent the plate 100 from moving when the screws 12 and 32 are inserted into the coupling holes 14 and 34 formed in the plate 100. The guide pin (not illustrated) is removed after the plate 100 is installed.

As an exemplary embodiment, at least one guide hole 40 may be formed in the head portion 30 in order to fix the head portion 30, and at least one guide hole 40 may also be formed in the body portion 10 in order to prevent swaying of the body portion 10.

Figure 4:
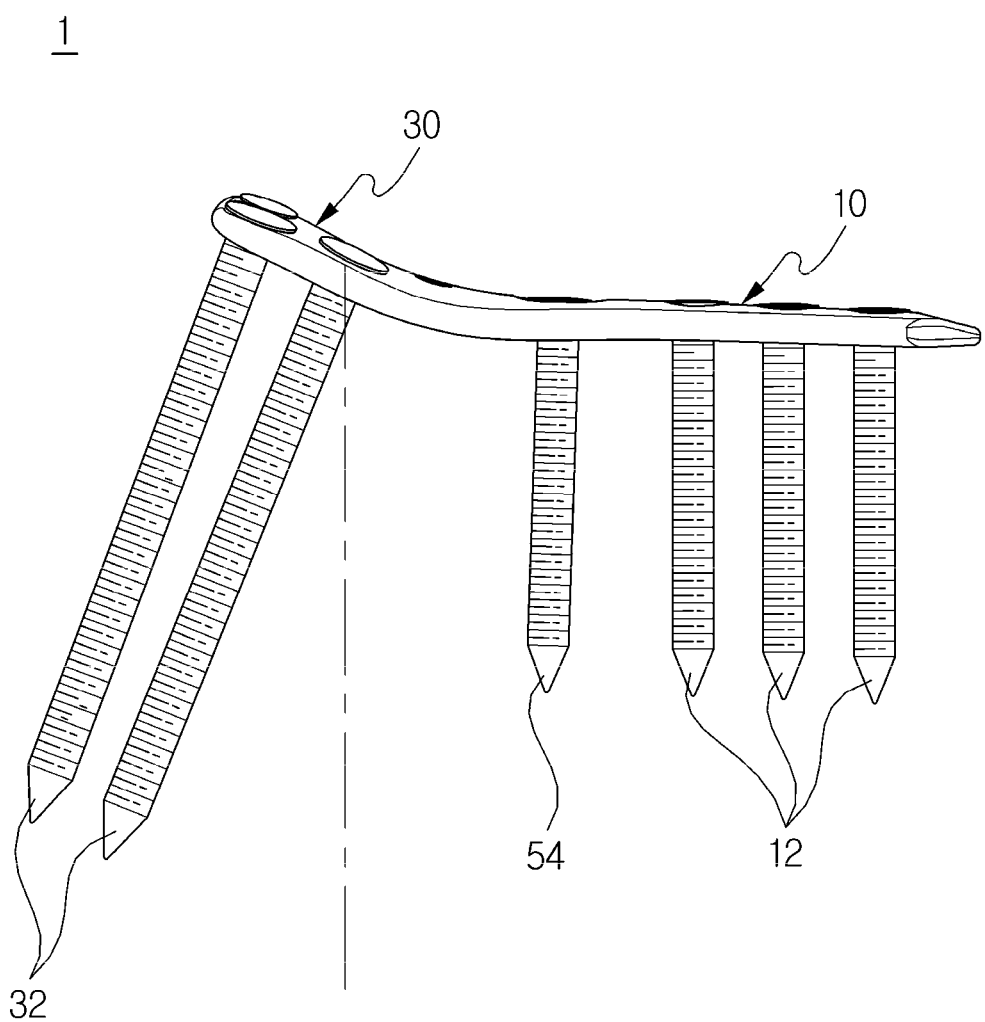
FIG. 4 is a view illustrating a coupled state of the fixing mechanism for a distal femur osteotomy according to the exemplary embodiment of the present invention.
Figure 5:
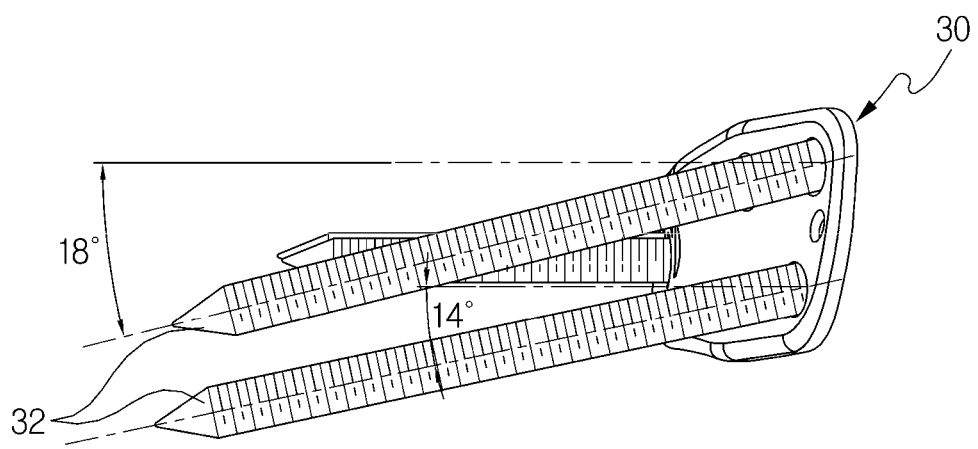
FIG. 5 is a view illustrating a coupling angle formed between screws coupled to the head portion according to the exemplary embodiment of the present invention.

FIG. 4 is a view illustrating a coupled state of the fixing mechanism for a closed distal femur osteotomy according to the exemplary embodiment of the present invention, and FIG. 5 is a view illustrating a coupling angle formed between screws coupled to the head portion according to the exemplary embodiment of the present invention.

Referring to FIGS. 4 and 5, the head portion 30 may be formed to have a predetermined inclination based on the body portion 10. In this case, the screw 32 coupled to the head portion 30 may have a predetermined inclination angle based on a vertical line. The inclination angle of the screw 32 may be naturally formed by the inclination of the head portion 30, and may be changed in accordance with an angle of the coupling hole 34.

As an exemplary embodiment, the coupling holes 34 may be formed along two rows and two columns, and the screw 32, which is coupled to the coupling hole 34 in a second row, may be formed to have an inclination angle of 16 to 18 degrees based on the vertical line.

In addition, the screws 32, which are coupled to the coupling holes 34 in the first and second rows, may be coupled to be directed toward a particular point. The reason is to stably maintain a coupled state with the lower femur 2b by preventing the screw 32 from penetrating the lower femur 2b when the head portion 30 is coupled to the lower femur 2b.

As an exemplary embodiment, the screw 32, which is inserted into the head portion 30, may form a predetermined angle based on a reference line when the screw 32 is coupled to the lower femur 2b. In a case in which the plate 100 stands on its side, the screw 32, which is coupled to a first row of the head portion 30, may have an inclination angle of 13 to 15 degrees based on a horizontal line, and the screw 32, which is coupled to a second row of the head portion 30, may have an inclination angle of 17 to 19 degrees based on the horizontal line.

A coupling angle of the screw 32 coupled to the head portion 30 may be variously modified in accordance with a thickness of the lower femur 2b.

Figure 6:
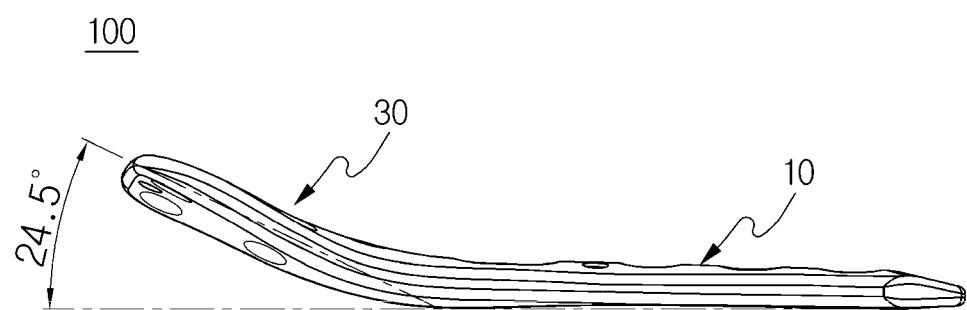
FIG. 6 is a view illustrating one side inclination of the head portion according to the exemplary embodiment of the present invention.
Figure 7:
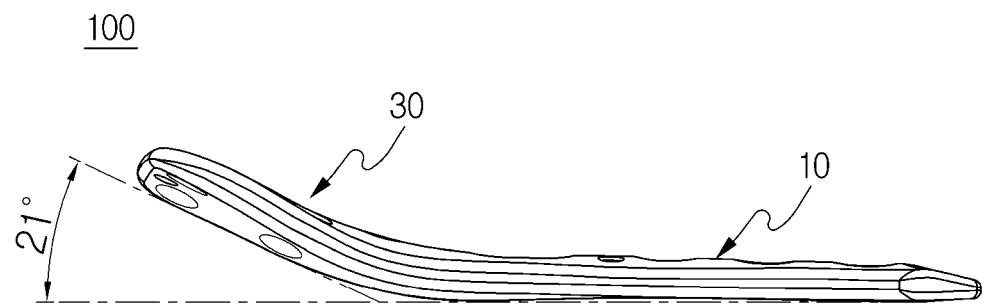
FIG. 7 is a view illustrating the other side inclination of the head portion according to the exemplary embodiment of the present invention.

FIG. 6 is a view illustrating one side inclination of the head portion according to the exemplary embodiment of the present invention, and FIG. 7 is a view illustrating the other side inclination of the head portion according to the exemplary embodiment of the present invention.

Referring to FIGS. 6 and 7, the head portion 30 according to the exemplary embodiment of the present invention may be formed to be twisted in a left or right direction based on the body portion 10. The reason is to bring the head portion 30 into close contact with the lower femur 2b in accordance with a skeleton structure of the femur 2. As the head portion 30 is twisted based on the body portion 10, an angle formed by one surface of the head portion 30 and an angle formed by the other surface of the head portion 30 may be different from each other.

As an exemplary embodiment, one surface of the head portion 30 may be formed to have an inclination angle of 20 to 22 degrees based on the body portion 10, and the other surface thereof may be formed to have an inclination angle of 24 to 26 degrees based on the body portion 10. An inclination angle of the head portion 30 may be variously modified in accordance with a shape of the lower femur 2b.

Figure 8:
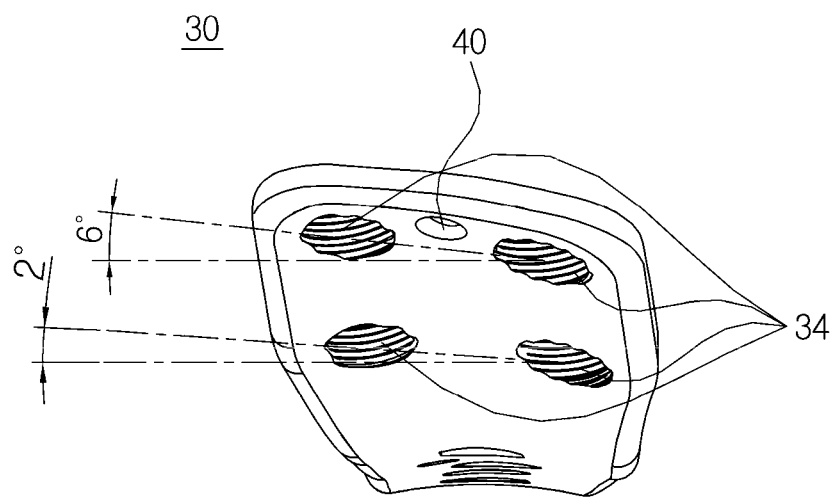
FIG. 8 is a view illustrating an inclination of a lower surface of the head portion according to the exemplary embodiment of the present invention.
Figure 9:
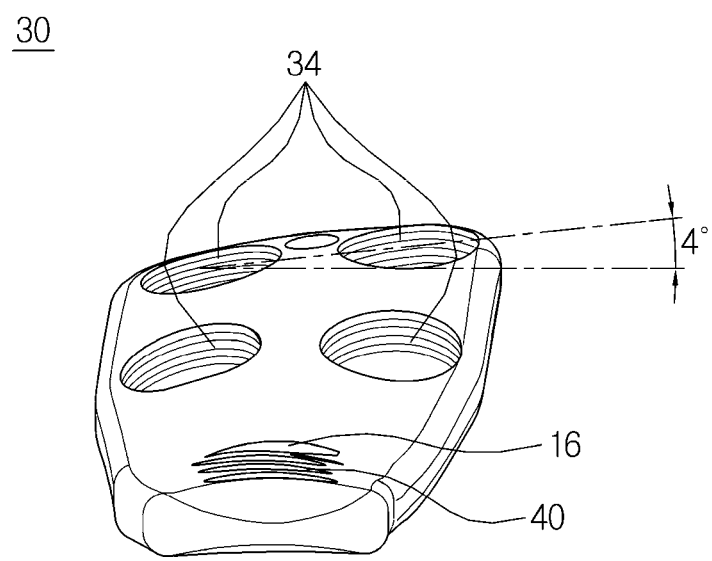
FIG. 9 is a view illustrating an inclination of an upper surface of the head portion according to the exemplary embodiment of the present invention.

FIG. 8 is a view illustrating an inclination of a lower surface of the head portion according to the exemplary embodiment of the present invention, and FIG. 9 is a view illustrating an inclination of an upper surface of the head portion according to the exemplary embodiment of the present invention.

Referring to FIGS. 8 and 9, the plate 100 may be formed to be curved so as to have a predetermined curvature so that the plate 100 may be in close contact with an outer circumferential surface of the femur 2. There is no limitation on the curvature of the plate 100, and the curvature of the plate 100 may be variously modified.

The head portion 30 of the plate 100 may be formed to have an upward inclination based on the body portion 10, and as described above, the head portion 30 may be formed to be twisted in the left or right direction based on the body portion 10.

A line, which connects central portions of the coupling holes 34 formed along the first column on the upper surface of the head portion 30, may be formed to have an inclination angle of 3 to 5 degrees based on the reference line, that is, the horizontal line.

In addition, a line, which connects central portions of the coupling hole 34 formed along the first column on the lower surface of the head portion 30, may be formed to have an inclination angle of 5 to 7 degrees based on the horizontal line, and a line, which connects central portions of the coupling holes 34 formed along the second column, may be formed to have an inclination angle of 1.5 to 2.5 degrees based on the horizontal line.

The reason why the inclination angles of the coupling holes 34 formed in the head portion 30 are different from one another is that a shape of the femur 2 does not have a predetermined curvature, and the head portion 30 having the coupling holes 34 may be coupled to the femur 2 by being in close contact with the femur 2.

As described above, according to the fixing mechanism for a distal femur osteotomy according to the exemplary embodiment of the present invention, it is possible to securely couple the plate and the bone by rotating the head portion.

In addition, since angles are formed at the head portion and thus the screws are not withdrawn from the bone, it is possible to reduce complications after the surgery.

The above description is simply given for illustratively describing the technical spirit of the present invention, and those skilled in the art to which the present invention pertains will appreciate that various modifications, changes and substitutions are possible without departing from the essential characteristic of the present invention. Accordingly, the exemplary embodiment disclosed in the present invention and the accompanying drawings are intended to not limit but describe the technical spirit of the present invention, and the scope of the technical spirit of the present invention is not limited by the exemplary embodiment and the accompanying drawings. The protective scope of the present invention should be construed based on the following claims, and all the technical spirit in the equivalent scope thereto should be construed as falling within the scope of the present invention.

The invention claimed is:

1. A fixing mechanism for a closed distal femur osteotomy, which is configured to be installed on a femur incised by the closed distal femur osteotomy, the fixing mechanism comprising:
a body portion having body coupling holes and an oblong hole, the oblong hole extending a predetermined length along a longitudinal direction of the body portion;
a head portion connected to the body portion and having ahead coupling holes;
body coupling screws inserted into the body coupling holes;
head coupling screws inserted into the head coupling holes; and
a sliding screw inserted into the oblong hole, the sliding screw being adjusted along the direction of extension of the oblong hole,
wherein the head portion comprises a head lower surface configured to directly contact a lower femur and a head upper surface opposite to the head lower surface, and the body portion comprises a body lower surface configured to directly contact an upper femur and a body upper surface opposite to the body lower surface,
wherein the head lower surface has a predetermined inclination angle in an upward direction based on the body lower surface,
wherein the head coupling screws inserted into the head portion are directed toward a particular single point,
wherein the head portion is tilted in a left or right direction with respect to the longitudinal direction,
wherein the head coupling holes are aligned in rows and columns, and
wherein a first imaginary line, which connects the centers of the head coupling holes formed along a first column on the upper head surface, is inclined 3 to 5 degrees with respect to a horizontal direction, which is vertical to the longitudinal direction.

2. The fixing mechanism of claim 1, wherein the head portion and the body portion are curved.

3. The fixing mechanism of claim 1, wherein a second imaginary line, which connects the centers of the head coupling holes formed along a first column on the lower head surface on the lower head surface, is inclined 5 to 7 degrees based on the horizontal direction.

4. The fixing mechanism of claim 3, wherein a third imaginary line, which connects the centers of the head coupling holes formed along a second column on the lower head surface, is inclined 1.5 to 2.5 degrees based on the horizontal direction.

5. The fixing mechanism of claim 1, wherein a first side of the head lower surface of the head portion is inclined 20 to 22 degrees based on the body portion, and a second side of the head lower surface is inclined 24 to 26 degrees based on the body portion.

6. The fixing mechanism of claim 1, wherein one lateral surface of the body portion is formed to have a predetermined inclination based on a lateral surface of the head portion.

7. The fixing mechanism of claim 6, wherein the predetermined inclination of the body portion is 7 to 9 degrees.

8. The fixing mechanism of claim 1, wherein a first one of the head coupling screws inserted into the corresponding coupling hole formed in the column is inclined 13 to 15 degrees based on an axis vertical to the lower head surface, and a second one of the head coupling screws inserted into the corresponding coupling hole formed in the column is inclined 17 to 19 degrees based in the axis.

9. The fixing mechanism of claim 1, further comprising: at least one guide hole and at least one guide pin, wherein the at least one guide hole is formed in the head portion or the body portion, and the at least one a-guide pin is inserted into the corresponding guide hole to temporarily fix the position of the head portion or the body portion.

10. The fixing mechanism of claim 1, wherein a first one of the head coupling screws inserted into the corresponding coupling hole formed in the column is inclined 16 to 18 degrees based on an axis vertical to the lower head surface.

* * * * *